(12) United States Patent
Zajac

(10) Patent No.: US 11,076,961 B2
(45) Date of Patent: Aug. 3, 2021

(54) COMPONENTS FOR ARTIFICIAL JOINTS

(71) Applicant: ARTHREX, INC., Naples, FL (US)

(72) Inventor: Eric Zajac, Naples, FL (US)

(73) Assignee: ARTHREX, INC., Naples, FL (US)

( * ) Notice: Subject to any disclaimer, the term of this patent is extended or adjusted under 35 U.S.C. 154(b) by 211 days.

(21) Appl. No.: 16/242,282

(22) Filed: Jan. 8, 2019

(65) Prior Publication Data

US 2019/0133771 A1     May 9, 2019

Related U.S. Application Data

(62) Division of application No. 15/095,512, filed on Apr. 11, 2016, now Pat. No. 10,182,917.

(51) Int. Cl.
*A61F 2/42* (2006.01)
*A61F 2/40* (2006.01)
(Continued)

(52) U.S. Cl.
CPC .......... *A61F 2/389* (2013.01); *A61B 17/1604* (2013.01); *A61F 2/30767* (2013.01); *A61F 2/3859* (2013.01); *A61F 2/3886* (2013.01); *A61F 2/461* (2013.01); *A61F 2/40* (2013.01); *A61F 2/4612* (2013.01); *A61F 2002/30011* (2013.01); *A61F 2002/30112* (2013.01); *A61F 2002/30332* (2013.01); *A61F 2002/30433* (2013.01); *A61F 2002/30604* (2013.01); *A61F 2002/30769* (2013.01); *A61F 2002/30878* (2013.01); *A61F 2002/30884* (2013.01); *A61F 2002/30892* (2013.01);
(Continued)

(58) Field of Classification Search
CPC .......... A61F 2/42; A61F 2/389; A61F 2/3859; A61F 2/3868; A61F 2002/2892; A61F 2/30767; A61F 2002/30433; A61F 2002/30884; A61F 2002/4619; A61F 2/3886; A61F 2/40; A61F 2/46; A61F 2/461; A61F 2/64; A61F 2/38; A61B 17/1604
See application file for complete search history.

(56) References Cited

U.S. PATENT DOCUMENTS 4,938,769 A   7/1990   Shaw et al.
4,986,833 A * 1/1991   Worland .................. A61F 2/40
                                                 623/19.11
(Continued)

FOREIGN PATENT DOCUMENTS

CN   101708138 A    5/2010
EP   2436341 A1    4/2012
(Continued)

OTHER PUBLICATIONS

European Search Report for European Patent Application No. 17166044.2, completed Aug. 4, 2017.

*Primary Examiner* — Seema Mathew
(74) *Attorney, Agent, or Firm* — Carlson, Gaskey & Olds, P.C.

(57) ABSTRACT

A component of an artificial joint according to an exemplary aspect of the present disclosure includes, inter alia, a base plate and a post selectively removable from the base plate. Further, an outer surface of the post includes a layer of the bone ingrowth material along substantially the entire length of the post.

12 Claims, 3 Drawing Sheets

(51) Int. Cl.
*A61F 2/38* (2006.01)
*A61F 2/30* (2006.01)
*A61B 17/16* (2006.01)
*A61F 2/46* (2006.01)

(52) U.S. Cl.
CPC ............. *A61F 2002/30925* (2013.01); *A61F 2002/4619* (2013.01); *A61F 2310/00407* (2013.01)

(56) References Cited

U.S. PATENT DOCUMENTS

| | | | |
|---|---|---|---|
| 5,019,103 A | 5/1991 | Van Zile et al. | |
| 5,116,375 A | 5/1992 | Hofmann | |
| 5,326,359 A | 7/1994 | Oudard | |
| 5,556,433 A | 9/1996 | Gabriel et al. | |
| 5,658,341 A | 8/1997 | Delfosse et al. | |
| 6,656,226 B2* | 12/2003 | Yoon | A61F 2/30907 623/23.23 |
| 7,578,850 B2 | 8/2009 | Kuczynski et al. | |
| 7,951,412 B2 | 5/2011 | Justin et al. | |
| 8,241,367 B2 | 8/2012 | Justin et al. | |
| 8,353,965 B2* | 1/2013 | Seitz, Jr. | A61F 2/3804 623/23.44 |
| 8,425,614 B2* | 4/2013 | Winslow | A61F 2/4003 623/19.11 |
| 10,034,756 B2* | 7/2018 | Landon | A61F 2/30734 |
| 10,307,260 B2* | 6/2019 | Heldreth | A61F 2/30767 |
| 10,835,382 B2* | 11/2020 | Habegger | A61F 2/3859 |
| 10,905,436 B2* | 2/2021 | nguyen | A61F 2/461 |
| 10,945,852 B2* | 3/2021 | Landon | A61F 2/30734 |
| 10,959,850 B2* | 3/2021 | Lee | A61F 2/30907 |
| 10,959,854 B2* | 3/2021 | Landon | A61F 2/389 |
| 2001/0039454 A1* | 11/2001 | Ricci | A61F 2/32 623/23.5 |
| 2003/0233149 A1 | 12/2003 | Hodorek | |
| 2004/0034432 A1* | 2/2004 | Hughes | A61L 27/16 623/20.28 |
| 2004/0122519 A1* | 6/2004 | Wiley | A61F 2/4081 623/18.11 |
| 2005/0154470 A1* | 7/2005 | Sekel | A61F 2/389 623/20.15 |
| 2007/0255412 A1* | 11/2007 | Hajaj | A61F 2/38 623/17.11 |
| 2009/0125114 A1 | 5/2009 | May et al. | |
| 2009/0162235 A1 | 6/2009 | Kita et al. | |
| 2009/0270994 A1 | 10/2009 | Schaefer et al. | |
| 2009/0326674 A1 | 12/2009 | Liu et al. | |
| 2010/0179662 A1* | 7/2010 | Verne | A61L 27/56 623/20.32 |
| 2011/0066246 A1 | 3/2011 | Ries et al. | |
| 2012/0101592 A1* | 4/2012 | Thomas | A61F 2/3603 623/23.55 |
| 2013/0190881 A1* | 7/2013 | Winslow | A61F 2/4014 623/19.11 |
| 2013/0218284 A1 | 8/2013 | Eickmann et al. | |
| 2013/0282135 A1* | 10/2013 | Sun | A61L 27/50 623/23.55 |
| 2013/0325136 A1* | 12/2013 | Thomas | A61B 17/157 623/20.32 |
| 2014/0172111 A1* | 6/2014 | Lang | A61F 2/389 623/20.32 |
| 2015/0359635 A1* | 12/2015 | Kita | A61F 2/28 623/23.6 |
| 2017/0042686 A1* | 2/2017 | Landon | A61F 2/30734 |
| 2018/0333267 A1* | 11/2018 | Landon | A61F 2/389 |
| 2019/0151102 A1* | 5/2019 | Hagen | A61F 2/3859 |
| 2019/0262012 A1* | 8/2019 | Collazo | A61B 17/17 |
| 2019/0282368 A1* | 9/2019 | Heldreth | A61B 17/8802 |
| 2019/0298525 A1* | 10/2019 | Wright | A61F 2/30767 |
| 2019/0298533 A1* | 10/2019 | Kane | A61L 27/58 |
| 2019/0343639 A1* | 11/2019 | Nguyen | A61F 2/30734 |
| 2020/0405908 A1* | 12/2020 | Kasinath | C09D 5/14 |

FOREIGN PATENT DOCUMENTS

| | | |
|---|---|---|
| EP | 2595571 B1 | 5/2013 |
| WO | 2006110896 A2 | 10/2006 |
| WO | 2012012726 A1 | 1/2012 |
| WO | 2012162180 A1 | 11/2012 |
| WO | 2015090834 A1 | 6/2015 |

* cited by examiner

COMPONENTS FOR ARTIFICIAL JOINTS

RELATED APPLICATIONS

This application is a divisional of prior U.S. application Ser. No. 15/095,512, filed Apr. 11, 2016, the entirety of which is herein incorporated by reference.

BACKGROUND

This disclosure relates to components for artificial joints and, more particularly, to artificial tibial components for total knee arthroplasty.

A total knee arthroplasty (TKA), also known as total knee replacement, is a surgical procedure in which parts of the knee joint are replaced with artificial parts (sometimes referred to as prostheses). In a typical TKA procedure, an artificial femoral component is attached to the femur, an artificial tibial component is attached to the tibia, and a spacer is provided between the femoral and tibial components. Known tibial components include a base plate supporting the spacer, and a post extending into a prepared opening in the tibia. The post is typically rigidly connected to the base plate.

SUMMARY

This disclosure describes components for artificial joints. The components can be used during total joint replacement procedures.

A component of an artificial joint according to an exemplary aspect of the present disclosure includes, inter alia, a base plate and a post selectively removable from the base plate. Further, an outer surface of the post includes a layer of the bone ingrowth material along substantially the entire length of the post.

In a further non-limiting embodiment, the layer of the bone ingrowth material on the post covers between 75% and 85% of the entire length of the post.

In a further non-limiting embodiment, the post projects from an inferior surface of the base plate.

In a further non-limiting embodiment, a layer of the bone ingrowth material is provided over substantially the entire inferior surface of the base plate.

In a further non-limiting embodiment, an inferior surface of the base plate is configured to rest on a prepared bone surface, and the post is configured to fit within a prepared bone opening.

In a further non-limiting embodiment, the base plate includes a pilot cylinder projecting from the inferior surface, the pilot cylinder receivable within a bore of the post.

In a further non-limiting embodiment, the base plate includes a plurality of pilot posts projecting from the inferior surface, the post projecting further from the inferior surface than the pilot posts.

In a further non-limiting embodiment, the post includes wings, and bone ingrowth material is provided on the wings.

In a further non-limiting embodiment, the wings each include planar anterior and posterior faces, and a layer of bone ingrowth material is provided on each of the anterior and posterior faces.

In a further non-limiting embodiment, the base plate includes a rim establishing a pocket, a fastener is configured to connect the base plate and the post, and the fastener rests flush with the pocket when connected to the post.

In a further non-limiting embodiment, the bone ingrowth material is provided by a layer of etched metal.

An artificial knee according to another exemplary aspect of the present disclosure includes, inter alia, an artificial femoral component, and an artificial tibial component including a base plate and a post selectively removable from the base plate. Further, an outer surface of the post includes a layer of the bone ingrowth material along substantially the entire length of the post. The artificial knee also includes a spacer located between the artificial femoral component and the artificial tibial component.

In a further non-limiting embodiment, the layer of the bone ingrowth material on the post covers between 75% and 85% of the entire length of the post.

In a further non-limiting embodiment, the post projects from an inferior surface of the base plate.

In a further non-limiting embodiment, a layer of the bone ingrowth material is provided over substantially the entire inferior surface of the base plate.

In a further non-limiting embodiment, the bone ingrowth material is provided by a layer of etched metal.

A method according to another exemplary aspect of the present disclosure includes, inter alia, removing a base plate from a post of a component of an artificial joint such that the post is left within bone. The post includes a layer of the bone ingrowth material along substantially the entire length of the post. Further, the method includes separating bone adjacent the bone ingrowth material from the post, and removing the post from the bone.

In a further non-limiting embodiment, the step of removing the base plate from the post includes loosening a fastener connecting the base plate and the post.

In a further non-limiting embodiment, the step of separating bone adjacent the bone ingrowth material includes using a reamer or a chisel to free the post from the bone.

In a further non-limiting embodiment, the layer of the bone ingrowth material on the post covers between 75% and 85% of the entire length of the post.

DETAILED DESCRIPTION

This disclosure describes components for artificial joints. The components can be used during total joint replacement procedures. For example, the components could be artificial tibial components for use during total knee arthroplasty procedures.

In some embodiments, a component of an artificial joint includes a base plate and a post selectively removable from the base plate. The post includes bone ingrowth material adapted to provide stability to the component via biological fixation. During an exemplary revisionary surgical procedure, for example, a surgeon can selectively remove the base plate from the post to increase access to the bone surrounding the post. The surgeon can then remove bone surrounding the post with increased precision, thus allowing the post to be removed with minimal bone loss.

Figure 1:
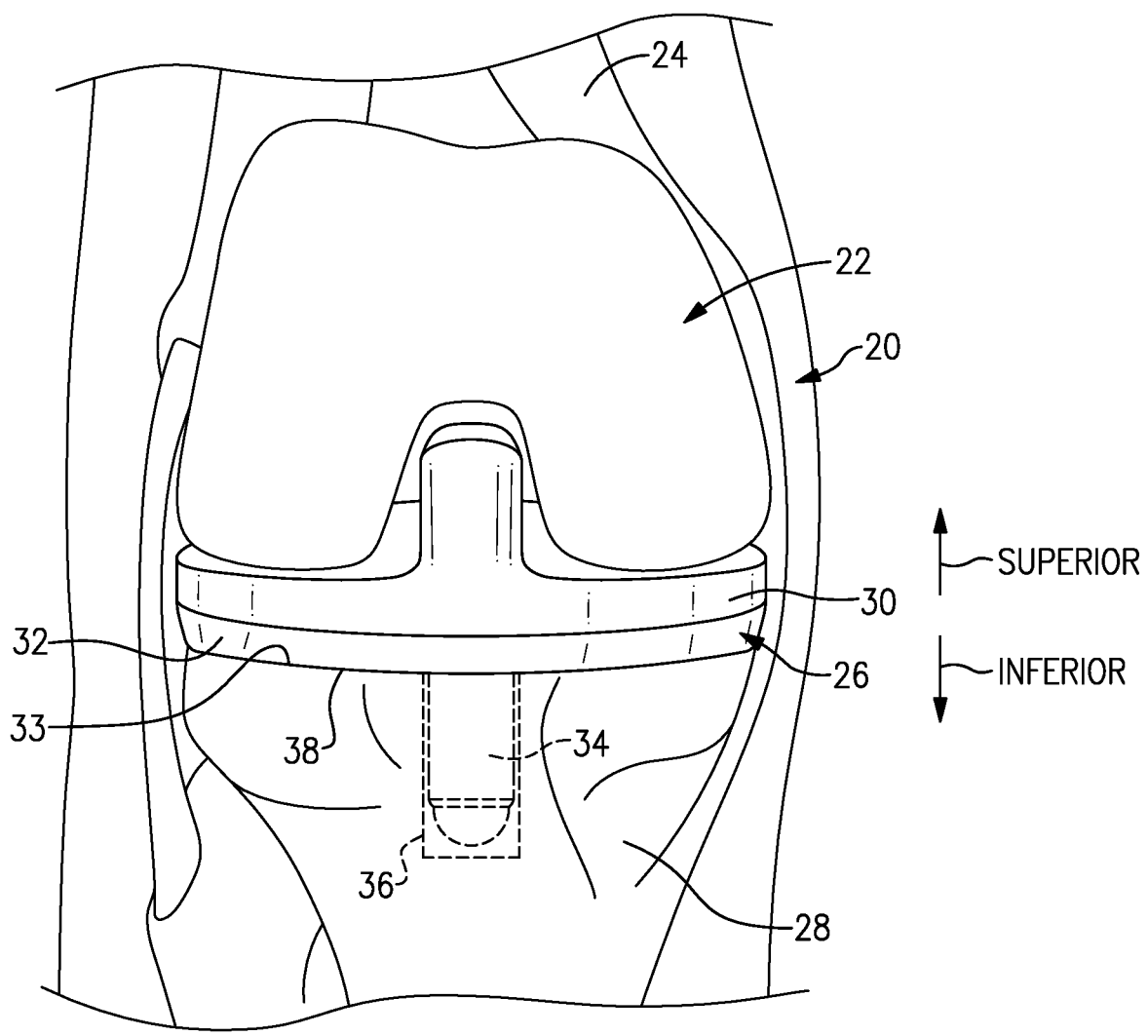
FIG. 1 illustrates an example artificial joint. In this example, the artificial joint is an artificial knee.

FIG. 1 illustrates an example artificial joint 20. In this non-limiting example, the artificial joint 20 is an artificial knee. While an artificial knee is specifically mentioned herein, this disclosure is not limited to artificial knee joints and can have applications in other parts of the body.

The artificial joint 20 includes an artificial femoral component 22 connected to a femur 24, an artificial tibial component 26 connected to a tibia 28, and a spacer 30 arranged between the artificial femoral component 22 and the artificial tibial component 26. In this non-limiting example, the artificial femoral and tibial components 22, 26 are made of metallic materials, and the spacer 30 is made of a plastic material. However, this disclosure is not limited to any particular materials.

In a non-limiting example, the artificial tibial component 26 is a tibial tray having a base plate 32 and a tibial post, or keel, 34. The superior, or top, portion of the base plate 32 is configured to support the spacer 30, and the inferior, or bottom, of the base plate 32 is configured to mate with a tibial plateau cut 33. The tibial post 34 projects from the base plate 32 in the inferior direction, and is received within a prepared opening 36 formed in the tibia 28. The "superior" and "inferior" directions are labeled in FIGS. 1 and 2A for purposes of explanation only.

Figure 2A:
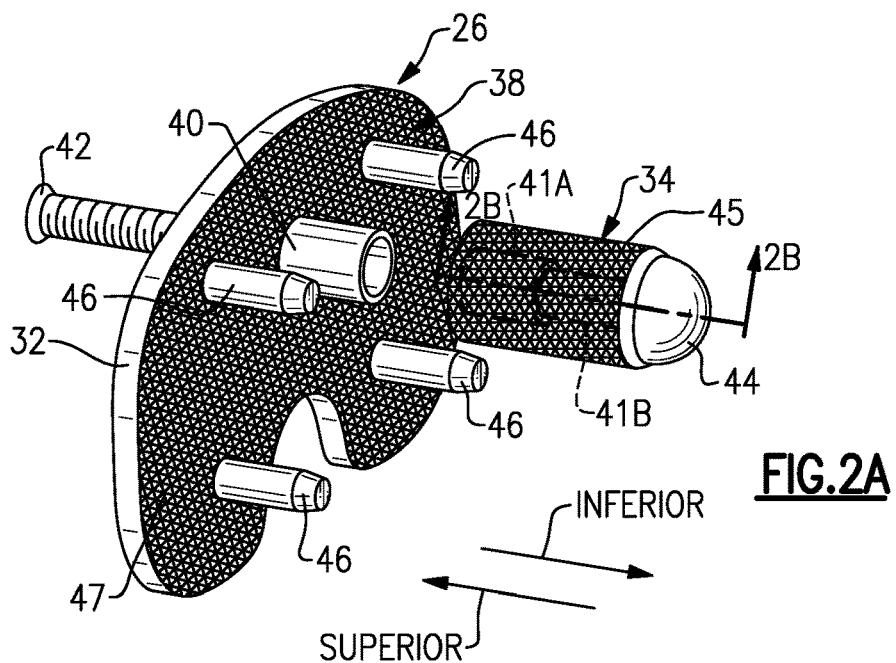
FIG. 2A is a perspective, exploded view illustrating an example component for an artificial knee. In this example, the component is a tibial tray.

FIG. 2A is a perspective, exploded view of the artificial tibial component 26. FIG. 2A illustrates the detail of the artificial tibial component 26 from an inferior perspective, and in particular shows the detail of the tibial post 34 and an inferior surface 38 of the base plate 32. The tibial post 34 projects in the inferior direction from the inferior surface 38. The tibial post 34 is sized to be press-fit in the prepared opening 36 (see FIG. 1), and is configured to support the artificial tibial component 26 relative to the tibia 28.

The base plate 32 and the tibial post 34 are selectively removable from one another. In other words, the tibial post 34 is "modular." In this non-limiting example, the tibial post 34 is connectable to the base plate 32 by a pilot cylinder 40. The pilot cylinder 40 serves to align the base plate 32 and tibial post 34.

Figure 2B:
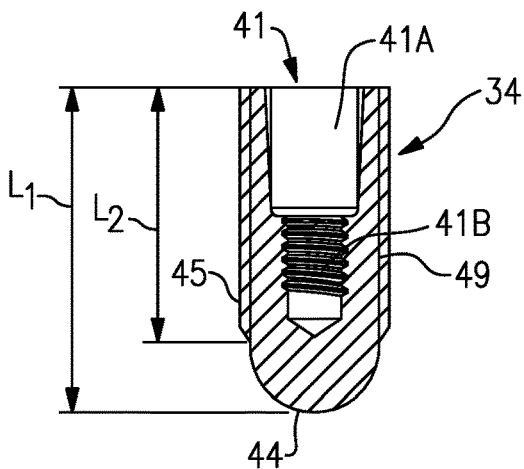
FIG. 2B is a cross-sectional view taken along line 2B-2B of FIG. 2A and illustrates the detail of an example tibial post.

FIG. 2B illustrates the interior details of the tibial post 34. In this non-limiting example, the tibial post 34 includes an interior bore 41 having a superior bore section 41A configured to receive the pilot cylinder 40 and an inferior bore section 41B configured to mate with a fastener 42. The superior bore section 41A may be tapered in the inferior direction and corresponds to a similar taper of the outer diameter of the pilot cylinder 40. However, the pilot cylinder 40 and superior bore section 41A need not be tapered in all examples.

The fastener 42 may be a threaded fastener configured to project beyond the inferior end of the pilot cylinder 40 and into the inferior bore section 41B of the tibial post 34. The inferior bore section 41B includes threads corresponding to those of the fastener 42. In a non-limiting example, the inferior bore section 41B has a smaller diameter than the superior bore section 41A. It should be understood that the tibial post 34 could be connected to the base plate 32 in other ways, and that this disclosure is not limited to the specific configuration shown in FIG. 2B.

Generally, the tibial post 34 includes a cylindrical body along substantially its entire length. The tibial post 34 further includes a rounded inferior end 44, although the inferior end 44 could be shaped differently. The overall size and shape, including the length and diameter, of the tibial post 34 may vary depending on the size of the tibia 28, for example.

In addition to the tibial post 34, the inferior surface 38 of the base plate 32 may include a plurality of pilot posts 46. The pilot posts 46 project in the inferior direction from the inferior surface 38 but do not project as far from the inferior surface 38 as the tibial post 34. Further, the pilot posts 46 each have a smaller diameter than the tibial post 34. The pilot posts 46 are received in prepared pilot openings in the tibia 28, and are used for initial alignment of the artificial tibial component 26 relative to the tibia 28. The pilot posts 46 may optionally be ribbed or threaded, although not necessary in all examples. Additionally, the pilot posts 46 themselves are not required in all examples.

The artificial tibial component 26 is configured to be connected to the tibia 28 without the use of bone cement. In other words, the artificial tibial component 26 is a "cementless" component. Instead of cement, the artificial tibial component 26 is connected to the tibia 28 via biological fixation. In particular, in a non-limiting example, the tibial post 34 and the inferior surface 38 are each provided with layers 45, 47 of bone ingrowth material, respectively.

The layers 45, 47 of bone ingrowth material are relatively porous, which allows bone to grow into the layers 45, 47. As bone grows into the layers 45, 47, the artificial tibial component 26 becomes biologically fixed to the tibia 28. The layers 45, 47 of bone ingrowth material may be fused to the tibial post 34 and the inferior surface 38, respectively. In other non-limiting examples, the layers 45, 47 are provided on the tibial post 34 and inferior surface 38 using a deposition coating process. The layer 45 is provided on an outer diameter 49 of the tibial post 34 along substantially the entire length of the tibial post 34, in yet another non-limiting embodiment.

In particular, with reference to FIG. 2B, the tibial post 34 has an overall length of $L_1$, and the layer 45 is provided along a length $L_2$, which is within a range of about 75% to about 85% of $L_1$. In a further non-limiting example, the length $L_2$ is about 80% of $L_1$. This disclosure is not limited to this particular range; however, providing this level of bone ingrowth material ensures a proper biological fixation while still allowing a surgeon to remove the bone adjacent the tibial post 34 if a revision is required (as further discussed below).

The layer 47 is provided on substantially the entire inferior surface 38 of the base plate 32. However, the locations adjacent the pilot cylinder 40 and the pilot posts 46 may exclude the layer 47. Thus, the layers 45, 47 allow bone adjacent the prepared opening 36 and the tibial plateau cut 33 to grow into the layers 45, 47, thereby biologically fixing the artificial tibial component 26 to the tibia 28.

In another non-limiting example, the layers 45, 47 of bone ingrowth material are provided by a chemically etched sheet of metallic material, such as titanium. One such bone ingrowth material is known as BioSync®. Other bone ingrowth materials, such as metallic foams, are also contemplated within the scope of this disclosure.

Figure 3:
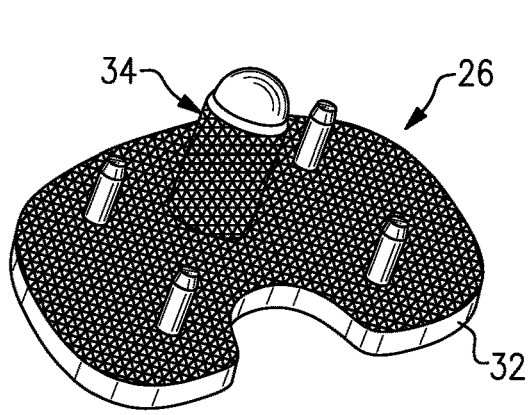
FIG. 3 is a bottom, perspective view of the component of FIG. 2A.

FIG. 3 illustrates the artificial tibial component 26 in an assembled condition from an inferior perspective. In the assembled condition, the threaded fastener 42 engages the tibial post 34, and the tibial post 34 is received over the pilot cylinder 40. In a non-limiting example, the artificial tibial component 26 is initially implanted into the tibia 28 in the assembled condition.

Figure 4:
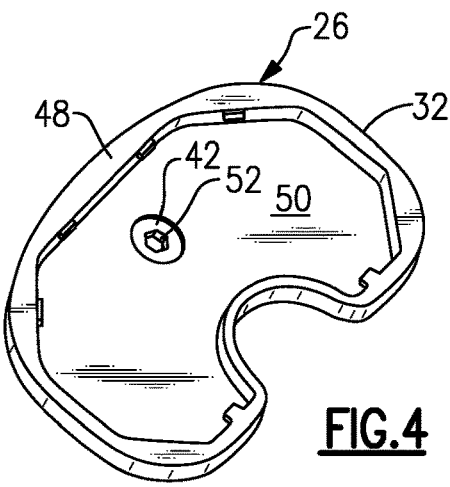
FIG. 4 is a top, perspective view of the component of FIG. 2A.

FIG. 4 illustrates the artificial tibial component 26 in the assembled condition from a superior perspective. The base plate 32 includes a rim 48 extending around a perimeter and establishing a pocket 50 therein. The pocket 50 receives a portion of the spacer 30 (see, e.g., FIG. 1). In the assembled condition, the fastener 42 is seated in the pocket 50. In this non-limiting example, the fastener 42 includes an internal socket 52, which may be hexagonally shaped, to mate with a correspondingly shaped driver (not shown). The fastener 42 sits flush with the pocket 50 to avoid interfering with the spacer 30.

Figure 5A:
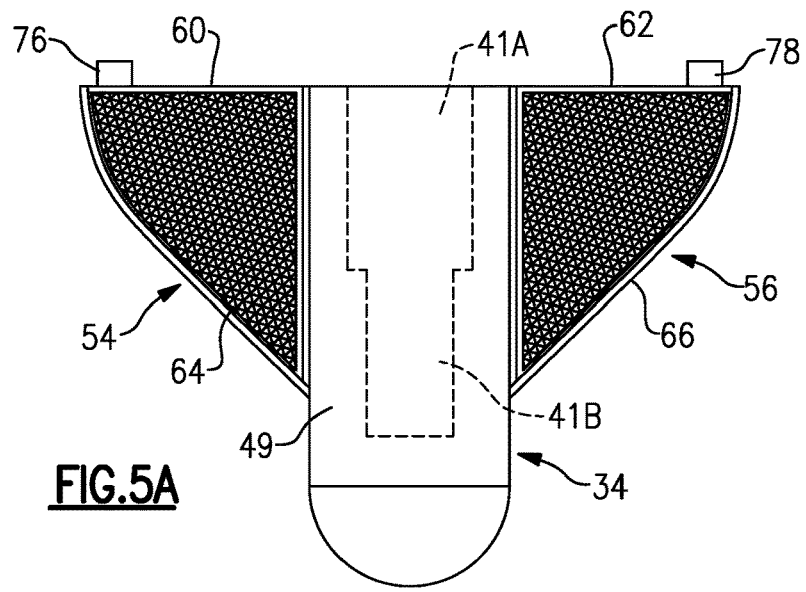
FIG. 5A is a front view of another example component for an artificial knee.
Figure 5B:
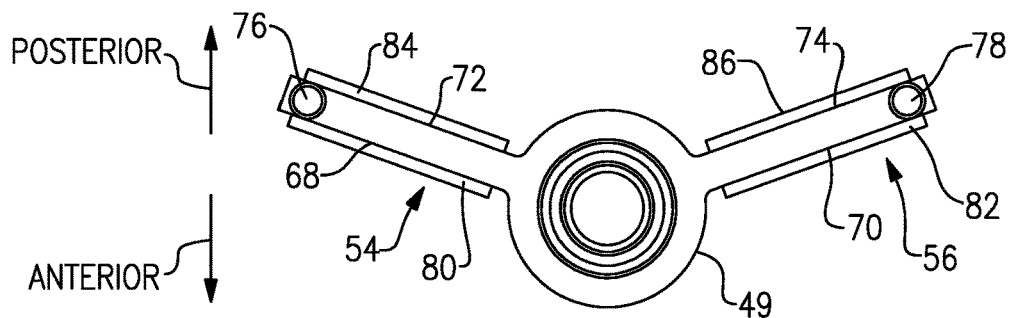
FIG. 5B is a top view of the example component of FIG. 5A.

FIGS. 5A and 5B illustrate another exemplary tibial post 34 that can be utilized as part of the artificial tibial component 26. In this non-limiting example, the tibial post 34 includes a pair of wings 54, 56. The wings 54, 56 project from the outer diameter 49 of the tibial post 34 in a posterior direction (the "anterior," or front, and "posterior," or rear, directions are labeled in FIG. 5B). The wings 54, 56 each have a superior surface 60, 62, an inferior surface 64, 66, anterior faces 68, 70, and posterior faces 72, 74. The superior surfaces 60, 62 are relatively planar and are configured to abut the inferior surface 38 of the base plate 32. The superior surfaces 60, 62 may include connection posts 76, 78 receivable in corresponding openings in the base plate 32. The inferior surfaces 64, 66 are provided with a smooth contour, beginning at a mid-point along the tibial post 34, and extending to the superior surfaces 60, 62.

In this non-limiting example, the anterior and posterior faces 68, 70, 72, 74 of the wings 54, 56 are provided with layers 80, 82, 84, 86 of bone ingrowth material. The anterior and posterior faces 68, 70, 72, 74 are relatively planar, which increases the ease of bonding the layers 80, 82, 84, 86 of bone ingrowth material thereto. In the non-limiting example of FIGS. 5A-5B, bone ingrowth material is not provided on the outer diameter 49 of the tibial post 34. However, bone ingrowth material could be provided on the outer diameter 49 of tibial post 34 in addition to the wings.

Some TKA procedures require a revisionary surgical procedure. A revisionary surgical procedure may be required in the case of infection (e.g., osteolysis) or if the artificial tibial component 26 otherwise loosens. During a revision, the entire artificial tibial component 26 is removed from the tibia 28.

Figure 6:
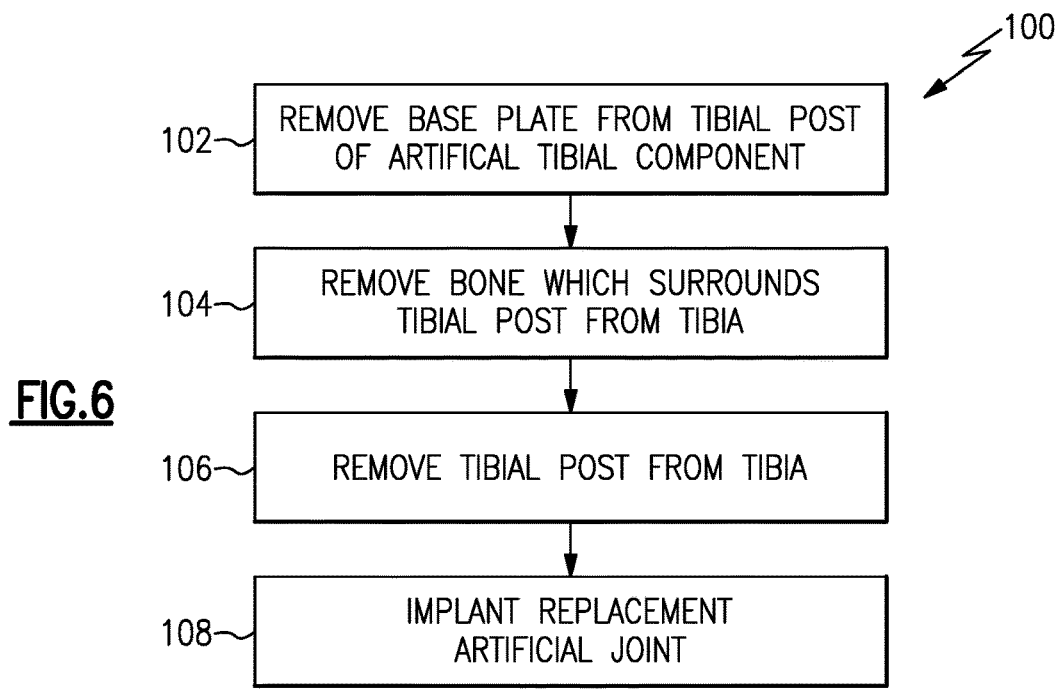
FIG. 6 schematically illustrates a method for performing a revisionary surgical procedure.

An exemplary method 100 of performing a revisionary surgical procedure is schematically illustrated in FIG. 6 for situations where the artificial tibial component 26 has previously been implanted as part of a TKA procedure. First, at block 102, a surgeon selectively removes the base plate 32 from the tibial post 34, such as by loosening the fastener 42, for example. When the base plate 32 is initially removed, the tibial post 34 remains in the tibia 28. By removing the base plate 32, the surgeon has increased access to the bone surrounding the tibial post 34 and/or the bone surrounding the wings 54, 56 (if wings are included).

Next, at block 104, the surgeon removes bone (using a surgical tool, such as a reamer or chisel, for example) that has grown into the bone ingrowth material with increased precision, which minimizes the amount of bone that must be removed from the tibia 28 in order to remove the tibial post 34. Once the ingrown bone has been separated from the tibial post 34, the tibial post 34 is freed and can be removed from the tibia 28 at block 106. The surgeon can then implant a replacement artificial joint at block 108.

Removal of prior art artificial joints can result in significant bone loss to the patient. This technical problem is addressed by the artificial joints discussed in this disclosure. For example, by providing bone ingrowth material on the tibial post 34 and/or the wings 54, 56 of the artificial tibial component 26, the stability and overall reliability of the connection between the artificial tibial component 26 and the tibia 28 is increased. Further, because the artificial tibial component 26 includes a modular tibial post 34, a surgeon can remove bone surrounding the tibial post 34 and/or wings 54, 56 with increased precision and minimal bone loss.

It should be understood that terms such as "anterior," "front," "posterior," "rear," "superior," "top," inferior," and "bottom" have been used herein for purposes of explanation only, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A method, comprising:
   removing a base plate from a post of a component of an artificial joint such that the post is left within bone, wherein the post has an overall length extending from a superior end of the post to an inferior end of the post, wherein the post includes bone ingrowth material covering the post from the superior end to a point along the post spaced-apart the superior end of the post by a distance between 75% and 85% of the overall length of the post, and wherein the post is free of bone ingrowth material between the point and the inferior end of the post;
   separating bone adjacent the layer of bone ingrowth material from the post; and
   removing the post from the bone.

2. The method as recited in claim 1, wherein the step of removing the base plate from the post includes loosening a fastener connecting the base plate and the post.

3. The method as recited in claim 2, wherein the base plate includes a rim establishing a pocket, and the fastener rests flush with the pocket when connected to the post.

4. The method as recited in claim 1, wherein the step of separating bone adjacent the layer of bone ingrowth material includes using a reamer or a chisel to free the post from the bone.

5. The method as recited in claim 1, wherein the inferior end of the post is rounded.

6. The method as recited in claim 1, wherein the post includes a cylindrical body along a majority of the overall length of the post.

7. The method as recited in claim 1, wherein the post projects further from an inferior surface of the base plate than all other structures of the component.

8. The method as recited in claim 1, wherein the bone ingrowth material is provided by a layer of etched metal.

9. The method as recited in claim 1, wherein the bone ingrowth material is provided on an outer diameter of the post.

10. The method as recited in claim 1, wherein the post includes a pair of wings projecting from an outer diameter of the post in a posterior direction.

11. The method as recited in claim 10, wherein the wings have superior surfaces lying in a common plane with the superior end of the post.

12. The method as recited in claim 10, wherein anterior and posterior faces of the wings include bone ingrowth material.

\* \* \* \* \*